United States Patent [19]

Petersen

[11] Patent Number: 5,260,019
[45] Date of Patent: Nov. 9, 1993

[54] METHOD AND APPARATUS FOR HEATING LIQUID SAMPLES, AND A CONTAINER FOR USE IN THE APPARATUS

[75] Inventor: Olav Petersen, Hillerod, Denmark

[73] Assignee: Hansens Verkstader AB, Kristianstad, Sweden

[21] Appl. No.: 662,496

[22] Filed: Feb. 28, 1991

Related U.S. Application Data

[63] Continuation of Ser. No. 254,676, Oct. 4, 1988, abandoned.

[30] Foreign Application Priority Data

Feb. 6, 1987 [DK] Denmark .............................. 605/87

[51] Int. Cl.⁵ .............................................. A23C 3/07
[52] U.S. Cl. .................................. 422/21; 198/474.1; 198/802; 219/10.55 A; 219/10.55 R; 422/74; 422/307; 435/290; 435/291; 436/23; 436/47
[58] Field of Search .................. 422/21, 63–65, 422/68.1, 74, 209, 307; 435/290, 291; 436/23, 47; 198/474.1, 802; 219/10.55 A, 10.55 R

[56] References Cited

U.S. PATENT DOCUMENTS

| | | | |
|---|---|---|---|
| 3,508,023 | 4/1970 | Ueda et al. | 219/10.55 |
| 3,759,303 | 9/1973 | Henrichs et al. | 141/1 |
| 3,998,030 | 12/1976 | Straub | 53/37 |
| 4,106,329 | 8/1978 | Takahashi et al. | 73/15 B |
| 4,444,723 | 4/1984 | Matsumaru et al. | 422/159 |
| 4,840,771 | 6/1989 | Williamson et al. | 422/104 |
| 4,961,489 | 10/1990 | Warkentin | 198/365 |

FOREIGN PATENT DOCUMENTS 0835896 7/1979 U.S.S.R. .
8601065 2/1986 World Int. Prop. O. .

Primary Examiner—James C. Housel
Assistant Examiner—Arlen Soderquist
Attorney, Agent, or Firm—Jacobson, Price, Holman & Stern

[57] ABSTRACT

In a method and an apparatus for heating large amounts of uniform milk samples (11) to about 40° C. preparatory to laboratory analyses, the samples are currently introduced into a carrousel-like machine. The machine has two axially offset levels (II and III), one (III) of which being a transport level and the other (II) a heating chamber (7) in which the samples are heated by high frequency energy, preferably in the form of microwaves. The samples are introduced mechanically into the heating chamber and maintained there during heating with current measurement of their temperature. When the temperature measurement shows that the samples have reached a desired temperature, they are released and fall back to the transport level and are transported out of the machine.

8 Claims, 4 Drawing Sheets

METHOD AND APPARATUS FOR HEATING LIQUID SAMPLES, AND A CONTAINER FOR USE IN THE APPARATUS

This is a continuation of application Ser. No. 07/254,676, filed Oct. 4, 1988, now abandoned which is the National Phase of PCT/DK88/00015, filed on Feb. 8, 1988.

The invention concerns a method of heating liquid samples which is particularly useful for heating milk to be subjected to treatment in an analyzer, where a large number of samples, which may have different initial temperatures and liquid amounts, are to be analysed, it being presupposed that when taken for analysis all samples have the same predetermined temperature.

In respect of milk samples, the samples to be heated are generally taken with at least one sample per milked cow and are sent, together with the milk supply, to the dairy where they are analysed. The result of the analysis forms the basis for the settlement with the supplier. Thus, it is a large number of samples which are to be treated each day.

To provide uniform start conditions for the analysis and also to condition the samples, these are to be heated to the same predetermined temperature before they are fed to the analyzer, as mentioned. The preheating apparatus used must typically be capable of supplying one sample every six seconds. Previously, heating of samples has been performed with preheating devices in the form of large systems consisting of a conveyor belt running through a water bath whose temperature has been regulated to the desired reference temperature. To obtain the desired temperature with certainty, the samples must be kept in the bath for a long time, and since finished samples are to be provided at a short interval of time, the baths must necessarily be large and will thus occupy much floor space. Further, it may be difficult to maintain the the required constant temperature over the entire bath. The known water baths also involve the drawback of evaporation of large amounts of water.

The object of the invention is to provide a method of the stated type which, while requiring little space, makes it possible to heat a large number of samples per unit of time exactly to a predetermined temperature, and also enables a construction of the apparatus necessary for performing the method which is acceptable to the user and the environments. This is achieved in that the method is performed with high frequency energy causing rapid and uniform heating of the whole liquid sample, and this energy impact is discontinued in that the container leaves the impact zone as soon as the liquid sample has obtained the desired temperature. The stated method also eliminates the drawback of the conventional heating method that the containers have to stay in water, which has an adverse effect on their identification marking.

The invention also concerns an apparatus for performing the stated method. Such an apparatus can be constructed as a compact structure which just occupies relatively little floor space.

One embodiment entails that the temperature sensors are in good contact with the containers when these are lifted up into the heating chamber, without interfering with the mounting of the containers on the platforms. The contact between the temperature sensors and the containers may be improved additionally by increasing the weight to increase the engagement pressure between the two parts. In addition, the weight has the effect of closing the container inlet opening when there is no container in the heating chamber, thereby preventing radiation of high frequency energy through this opening.

A simple and effective embodiment of the holding means for maintaining the platforms in the lifted position and for releasing them from this position to remove the containers from the heating chamber under the action of gravity when the reference temperature has been reached.

The invention further concerns a container for use in the stated apparatus and consisting of a material of poor heat conduction, and a metal disc of good heat conduction in the bottom or cover. Good heat transfer contact is obtained between the temperature sensor of the apparatus and the sample liquid in the container irrespective of the poor heat conductivity of the container material. Seen from a production-technical point of view, it is usually most expedient that the metal disc is arranged in the container cover. The fact that the containers will then have to be arranged bottom up on the platforms involves the additional advantage that the reversal of the container provides a certain stirring effect in and thus greater uniformity of the sample liquid.

BRIEF DESCRIPTION OF THE FIGURES

The invention will be explained more fully below with reference to the drawing, in which

In the drawing, 1 is a stationary machine frame, in relation to which an assembly 2, which constitutes the major part of the apparatus, can move in the direction indicated by an arrow. As shown in FIGS. 2 and 3, the machine frame 1 and the assembly 2 may be constructed as a circular unit, the assembly 3 being rotatable about a bearing in the machine frame. This arrangement represents a preferred embodiment, and the apparatus will be described in this form below. The centre of the machine frame incorporates a central pipe 16, FIG. 2, carrying a bearing 17 in which the assembly 2 is rotatably journalled. The assembly 2 is provided with a toothed rim 15 which meshes with a gear wheel 14 arranged on the shaft of an engine 12. The engine 12 is firmly positioned in connection with the machine frame 1. When the engine is activated, the entire assembly 2 consequently rotates with respect to the machine frame about the bearing 17. The shaft of the engine 12 also carries a transport wheel 13 so constructed as to be capable of transporting sample containers 11 containing the sample to be heated from a feed belt 18 into the assembly 2. The transport wheel 13 is coupled to the assembly 2 such that an introduced sample container will be delivered on one of a plurality of platforms having lifting means, whose arrangement will be explained more fully later. If the feed belt 18 is full, the assembly 2 will consequently be filled with sample containers when the engine 12 is activated. The toothed rim 15 is moreover coupled with a transport wheel 20 adapted to transport the sample containers from the assembly 2 out on to a discharge belt 19 which can transport the sample containers away.

This transport wheel is arranged so that the sample containers traverse such a great part of an entire rotation of the assembly 2 as is geometrically possible.

Figure 2:
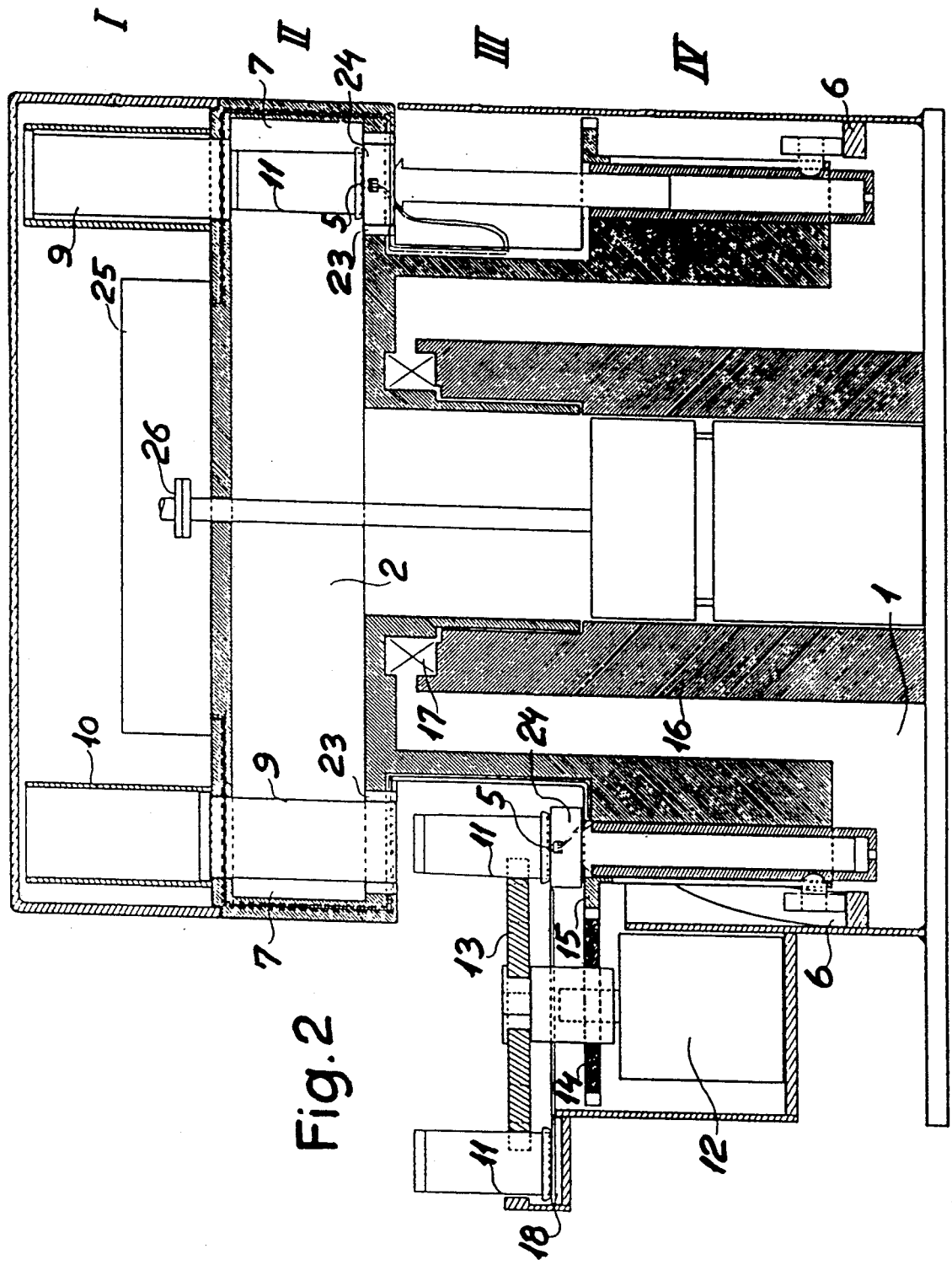
FIG. 2 is a vertical section through the entire apparatus.
Figure 3:
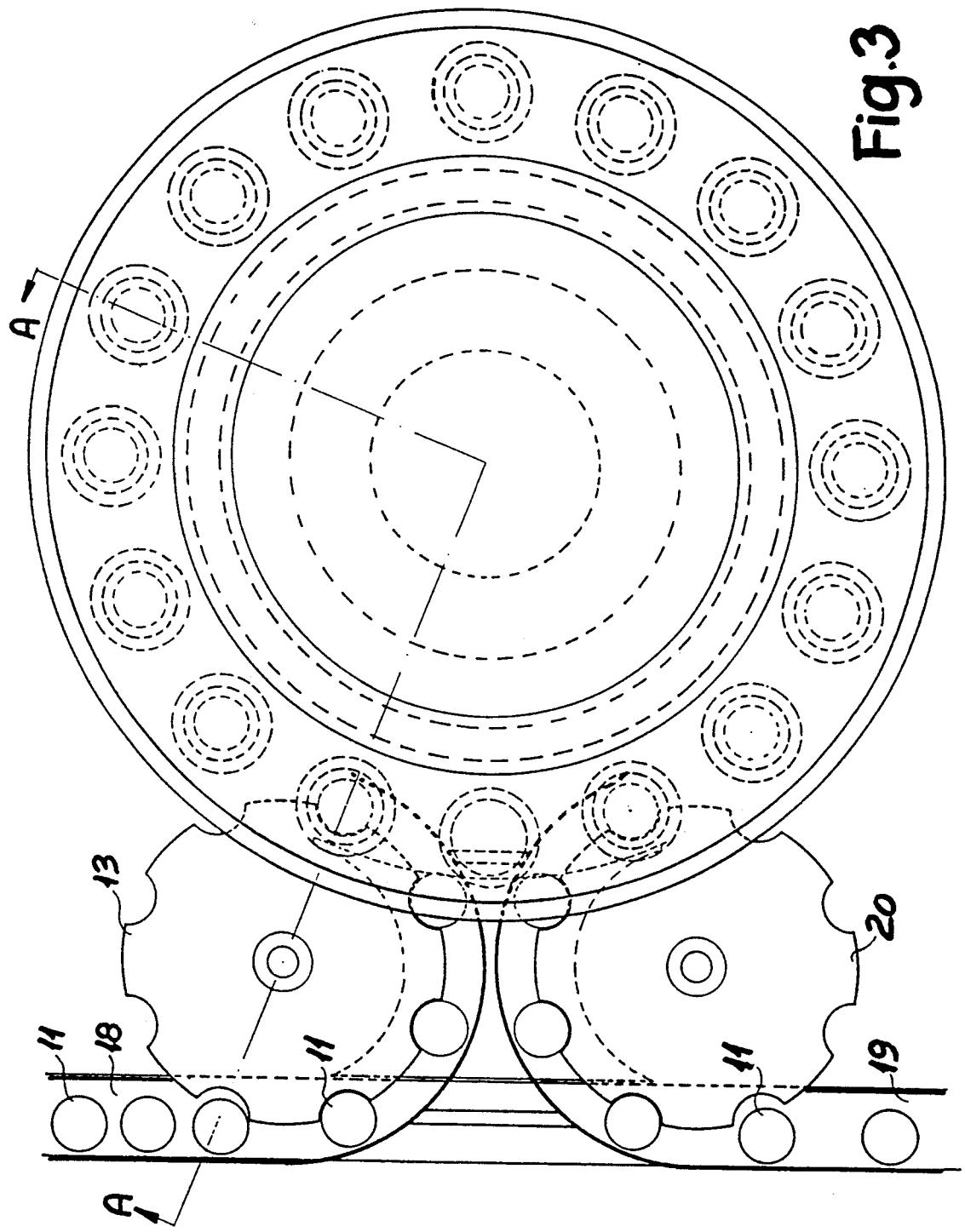
FIG. 3 is a top view of the transport mechanism of the apparatus.

As shown in FIG. 2, the assembly 2 is divided into four "floors" or levels I-III. Level I is the top one and is called weight chamber level for reasons given below. Level II is called heating chamber level below. It constitutes the part in which the material to be heated is placed and contains a high frequency apparatus which can deposit energy in materials having suitable dielectric properties.

In a preferred embodiment, the high frequency apparatus itself is formed by a microwave oven, but nothing prevents the use of a dielectric high frequency heater. In the first case, the heating chamber will be in the form of a suitably dimensioned space where the high frequency energy is fed from a wave conductor. In the second case, the heating chamber is formed as a co-axial capacitor which is incorporated in an oscillation circuit in the power generator.

Level III is called transport level below and is the level where the sample containers are present when they have just been introduced into the apparatus and when, after completed heating, they are transported out of the apparatus. Level IV is called elevator level and contains the lifting means and guides which just allow axial movements of the lifting means, and means for performing this movement.

Figure 1:
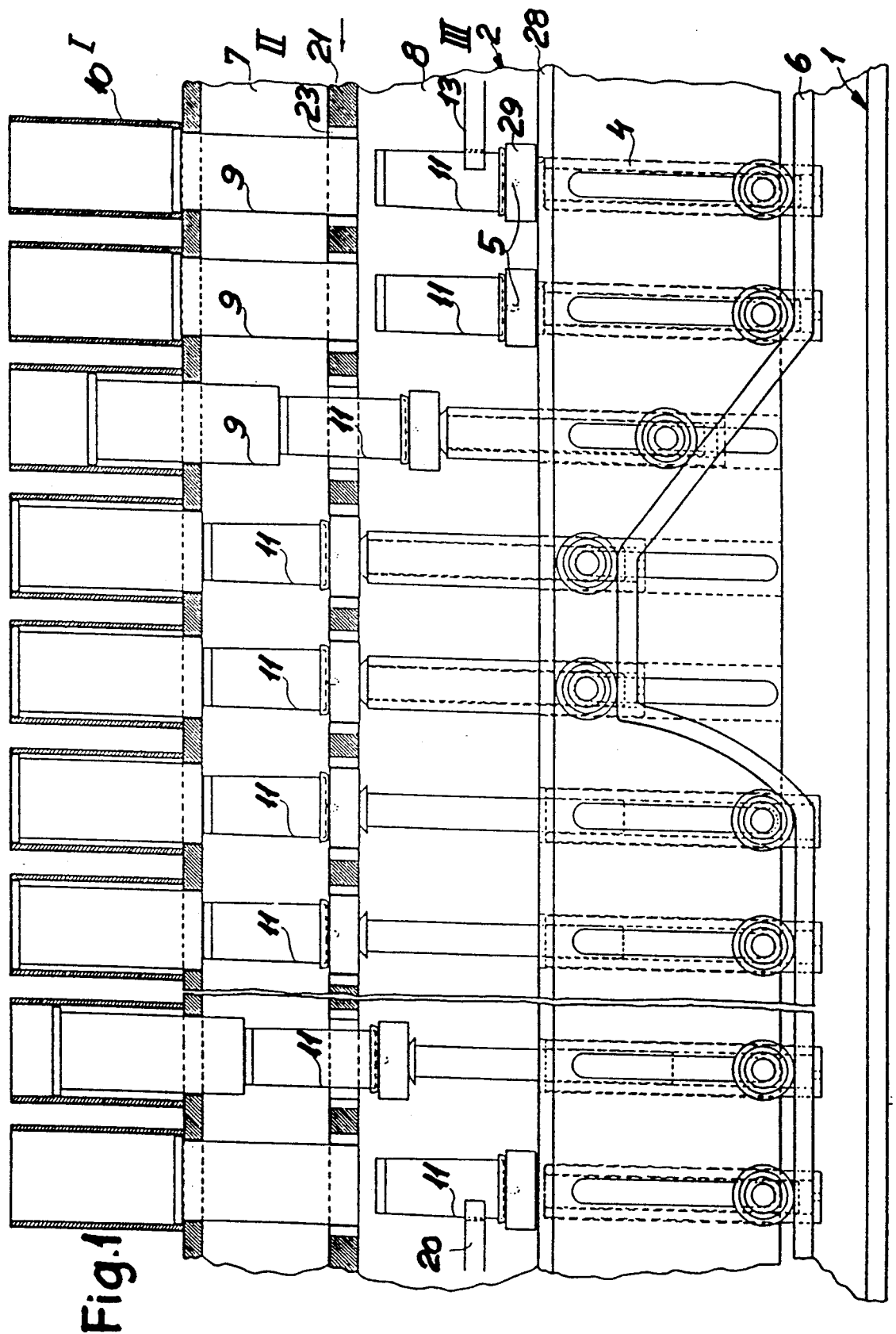
FIG. 1 is a developed vertical section through part of the embodiment of the apparatus of the invention.

It is schematically shown in FIG. 1 how the sample containers can be transported through the apparatus. Sample containers 11 are shown in a plurality of different positions during the transport through the apparatus. To the extreme right, a container has just been delivered from the transport wheel and stands on its platform 29. This is shown in more detail in FIG. 4, together with the associated lifting means 24 and other components. The lifting means 24 may be moved vertically by means of a ramp 6 on the machine frame and thus be lifted from the elevator level IV upwardly toward the heating chamber level II, so that the container is introduced into a heating chamber 7 when the assembly 2 is moved in the direction of the arrow. A holding mechanism, generally designated by 23, serves to retain the lifting means in its top position and may e.g. be released by an electric magnet. The lifting means will be retained by the holding means 23 in a position where the sample container 11 is present in the heating chamber when it is no longer under the action of the ramp 6. The heating chamber receives power from the high frequency apparatus, and sample containers 11 present in the heating chamber will therefore be heated.

Co-axially with each sample position a weight 19, guided by a weight guide 10, is present in level I. When no sample container is present in the sample position in question, the weight is in its lowermost position and thus closes the access to the heating chamber, resulting in a considerable reduction in unintentional radiation of high frequency energy to the surroundings. When a sample container is introduced into the heating chamber by its lifting means, the container displaces the weight so that this partly moves upwardly in its guide and partly subjects the container to the load of its weight, so that the container is maintained steadily and is brought into good heat-conduction contact with a temperature sensor 5 disposed at the top end of the lifting means. When the holding mechanism 23 is released, the weight finally contributes to rapid ejection of the container from the heating chamber and causes it to be closed again to the surroundings.

An electronic unit, fed with power via slip rings, is placed in level I. The electronic unit contains a circuit for each sample position, said circuit comparing a signal from each temperature sensor with an adjustable reference signal adjusted to a value which corresponds to the signal value of the temperature sensor for the desired temperature of the samples. The comparator circuit may be formed by an operational amplifier of a generally known type, which receives the reference signal on its one input and receives the signal from the temperature sensor on its other input. A suitable temperature sensor is e.g. a thermistor of a type which is used for disposable thermometers for medical purposes. Such a thermistor is accurately calibrated precisely in the temperature range which is relevant here, viz. 40° to 42° C., and such precise calibration is desirable, particularly if it is desired to use a common reference for all the comparator circuits. The comparator circuit has its output connected to an amplifier which controls the holding mechanism such that it maintains the sample in the heating chamber until the temperature sensor indicates that the sample has obtained the temperature prescribed by the reference. The holding mechanism 23 is so constructed in a preferred embodiment that it has to be fed with power to release the sample so that it is ejected from the heating chamber, and in this case a monostable multivibrator may be interposed between the comparator circuit and the amplifier, said multivibrator being triggered by the comparator circuit when the sample has reached the desired temperature so that the holding mechanism is just fed with power for a period of sufficient duration to ensure certain release of the sample.

Figure 4:
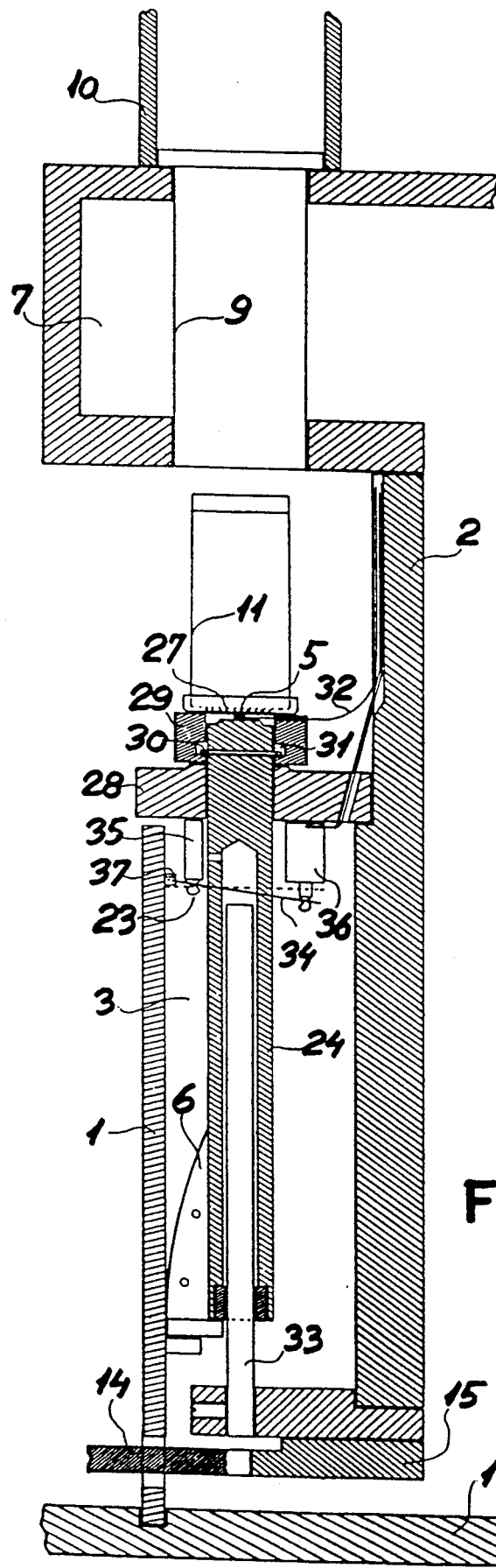
FIG. 4 is a vertical section through one of the lifting mechanisms of the apparatus.

FIG. 4 shows a preferred embodiment of the means to introduce the samples into the heating chamber and to maintain them as well as to release them when they have reached the desired temperature.

The arrangement is shown in the state it has when a sample has just been delivered from the transport wheel. As mentioned, the sample is delivered on a platform, which is ring-shaped and stands, in its position of rest, on a partition between the elevator level IV and the transport level III. The platform 29 is kept radially in place by the lifting means 24 which extends through the hole in the centre of the platform with a loose fit. Axially, the platform is retained with respect to the lifting means by a locking ring 30 which projects into a recess in the inner side of the platform, said recess being so shaped as to allow a certain axial movement. On the platform, the temperature sensor 5 is placed with the active sensor element in the centre of the centre hole of the platform and is so loosely suspended as to be disposed below the top side of the platform in its position of rest and thus allows unobstructed delivery of the sample on the platform. The temperature sensor is connected to the electronic unit by a lead 32. The lifting means 24 is guided by a guide in the partition 28 and by a guide column 33 so that while being readily axially movable it is precisely guided and controlled. The ramp 6 on the machine frame cooperates with the lifting means 24 as shown. When the assembly 2 is rotated with respect to the machine frame, the lifting means will thus be displaced vertically, so that, owing to the allowed axial movement between platform and lifting means, the temperature sensor will be pushed upwardly toward and be brought into good heat conducting contact with a metallic membrane provided on the cover of the sample container, and the container will additionally be moved up into the heating chamber against the load of the weight 9. A clamp plate 34, loosely suspended from a rod 35, allows movement of the lifting means in an upward direction, but opposes by clamping effect any movement of the lifting means in a downward direction and thus causes the sample to be retained in the heating chamber, also when the lifting means is no longer under the action of the ramp 6. The clamp plate 34 is also mechanically connected to a solenoid 36. When this solenoid is energized, it lifts the clamp plate and thus causes release of the clamping effect of the clamp plate, so that the sample is ejected from the heating chamber under the load of the weight 9. The fall of the sample toward the transport level is cushioned by the air around the column 33, and to provide suitable cushioning a suitable blow-off hole may optionally be formed in the lifting means. The solenoid is connected to the electronic unit and will be activated when the temperature sensor indicates that the sample has reached the temperature prescribed by the reference. It is important to ensure that all samples are present in the transport level when they are to be transported out of the apparatus, even under possible error conditions. A boss 37, is so placed on the machine frame as to cooperate with the clamp plate to forcibly cancel its clamping effect so late in the cycle that all samples should have been ejected after the normal function of the machine. In FIG. 4, the toothed rim 15 and the gear wheel 14 are shown disposed below the bottom of the assembly 2. When these components are positioned as shown, the transport wheels 13 and 20 are synchronized with the carrousel without additional gearing between gear wheel and transport wheel to obtain correct geometry.

The invention is not restricted to the special embodiment shown and described, since its details may be modified in many ways within the scope of the invention, just as the method and the apparatus of the invention may be used for heating other liquids than milk.

I claim:

1. A method of individual heating of liquid samples contained in containers to a predetermined reference temperature comprising the steps of:
    continuously and separately introducing the containers containing the individual liquid samples into a single heating chamber for a plurality of containers;
    performing the heating in said heating chamber by high frequency energy;
    monitoring the temperature of each individual liquid sample contained in said containers;
    comparing the monitoring temperature with the reference temperature;
    individually removing each container containing the individual sample from the single heating chamber when the contained liquid sample has reached the reference temperature together with the steps of successively lifting the containers containing the individual samples up into the heating chamber from a transport means extending below and along the heating chamber; and releasing each container containing the individual sample for return to the transport means by means of gravity when its content has reached the reference temperature.

2. A method according to claim 1, wherein the heating chamber and the transport means move as a unit in a ring-shaped path.

3. An apparatus for heating liquid samples in individual containers, comprising:
    a single heating chamber for a plurality of containers;
    means for separately introducing the individual containers containing the liquid samples into said heating chamber;
    means for heating by high frequency energy;
    means for monitoring the temperature of each liquid sample contained in said containers;
    means for comparing the monitoring temperature with a reference temperature;
    means for individually removing each container containing the individual sample from the single heating chamber when the liquid has reached the reference temperature together with a ring-shaped transport means rotatable about a vertical axis and formed with spaced, vertically movable platforms for supporting the containers containing the individual sample;
    means for lifting each platform so that the containers containing the individual sample are moved up into the heating chamber through an opening in the bottom of the heating chamber; and
    releasable holding means for holding each container containing the individual sample in the heating chamber until the contained individual sample has reached the reference temperature.

4. An apparatus according to claim 3, further comprising a temperature sensor so placed on each platform as to be in heat transfer contact with a container placed on the platform.

5. An apparatus according to claim 4, wherein each platform is constituted by a carrier ring and a rod-shaped, axially movable lifting means whose upper end part extends up into and is so connected with the ring that the two parts have limited axial movability in relation to each other, said temperature sensor being so placed on the end of the lifting means as to be present below and above the support face of the carrier ring, respectively, when the lifting rod is in its bottom position and top position, respectively, with respect to the carrier ring, a stationary ramp being provided to cause upward movement of the rod-shaped lifting means.

6. An apparatus according to claim 3, wherein the heating chamber is upwardly defined by a ceiling plate having openings co-axial with the openings in the bottom, and a weight is axially movable in each of said ceiling openings, said weight extending through or into and essentially filling both of the co-axial openings in its bottom position.

7. An apparatus according to claim 3, wherein each of the releasable holding means is formed by a clamp plate which is tiltable about a horizontal axis and is in contact with the rod-shaped lifting means in its active state such as to allow upward, but to prevent downward movement of it, a solenoid, when energized, being adapted to bring the clamp plate into an inactive state in which it allows downward movement of the lifting means.

8. The apparatus of claim 3, wherein the container containing the individual sample consists essentially of a material of poor heat conduction and has a heat conducting area of a material of good heat conduction.

* * * * *